United States Patent
Ma (10) Patent No.: US 10,768,690 B2
(45) Date of Patent: Sep. 8, 2020

(54) MOTION-SENSING INTERACTIVE SYSTEM AND MOTION-SENSING INTERATION METHOD

(71) Applicant: Meta Technologies Inc., Irvine, CA (US)

(72) Inventor: Weixun Ma, Zheji-ang (CN)

(73) Assignee: META TECHOLOGIES INC., Irvine, CA (US)

( * ) Notice: Subject to any disclaimer, the term of this patent is extended or adjusted under 35 U.S.C. 154(b) by 268 days.

(21) Appl. No.: 15/567,229

(22) PCT Filed: Apr. 18, 2016

(86) PCT No.: PCT/CN2016/079535
§ 371 (c)(1),
(2) Date: Oct. 17, 2017

(87) PCT Pub. No.: WO2016/165665
PCT Pub. Date: Oct. 20, 2016

(65) Prior Publication Data
US 2018/0107267 A1    Apr. 19, 2018

(30) Foreign Application Priority Data

Apr. 17, 2015   (CN) .......................... 2015 1 0185080

(51) Int. Cl.
*G06F 3/01* (2006.01)
*G06F 3/0346* (2013.01)
*A61B 5/11* (2006.01)

(52) U.S. Cl.
CPC ................ *G06F 3/011* (2013.01); *A61B 5/11* (2013.01); *A61B 5/1116* (2013.01); *G06F 3/017* (2013.01); *G06F 3/0346* (2013.01)

(58) Field of Classification Search
CPC ........ G06F 3/011; G06F 3/017; G06F 3/0346; A61B 5/11; A61B 5/1116
See application file for complete search history.

(56) References Cited

U.S. PATENT DOCUMENTS

| 8,688,375 B2 * | 4/2014 | Funk .................... G01C 21/165 340/995.19 |
| 2007/0072674 A1 | 3/2007 | Ohta et al. |

(Continued)

FOREIGN PATENT DOCUMENTS

| CN | 101579238 A | 11/2009 |
| CN | 102441277 A | 5/2012 |

(Continued)

OTHER PUBLICATIONS

World Intellectual Property Organization, International Search Report for International Application No. PCT/PCT/CN2016/079535, dated Jun. 17, 2016, pp. 1-6.

*Primary Examiner* — Regis J Betsch
(74) *Attorney, Agent, or Firm* — SoCal IP Law Group LLP; Nikki M. Dossman; Steven C. Sereboff (57) ABSTRACT

Provided is a somatosensory control device (100), comprising an intelligent electronic device (20) and at least one somatosensory control device (10) wirelessly connected and paired. The at least one somatosensory control device (10) comprises a posture sensing module (12), a transmission module (14) and a power supply module (16). The posture sensing module (12) is configured to sense motion posture data. The intelligent electronic device (20) is configured to receive the motion posture data and recognize corresponding motion according to the motion posture data to perform corresponding operations. A somatosensory control method is further provided.

9 Claims, 6 Drawing Sheets

(56) References Cited

U.S. PATENT DOCUMENTS

| | | | |
|---|---|---|---|
| 2010/0001893 A1* | 1/2010 | Kim | G08C 17/02 341/176 |
| 2014/0176422 A1* | 6/2014 | Brumback | A61B 5/0015 345/156 |
| 2015/0168152 A1* | 6/2015 | Stensland | G01B 21/22 702/150 |
| 2017/0206673 A1* | 7/2017 | Kawamoto | G06T 7/70 |

FOREIGN PATENT DOCUMENTS

| | | |
|---|---|---|
| CN | 103186256 A | 7/2013 |
| CN | 103377541 A | 10/2013 |
| CN | 104898827 A | 9/2015 |
| CN | 104898828 A | 9/2015 |
| CN | 104898829 A | 9/2015 |
| WO | 2016165665 A1 | 10/2016 |

\* cited by examiner

MOTION-SENSING INTERACTIVE SYSTEM AND MOTION-SENSING INTERATION METHOD

This patent claims priority from International PCT Patent Application No. PCT/CN2016/079535, filed Apr. 18, 2016 entitled, "MOTION-SENSING INTERACTIVE SYSTEM AND MOTION-SENSING INTERACTION METHOD", which claims priority to Chinese Patent Application No. 201510185080, filed Apr. 17, 2015 entitled, "SOMATOSENSORY INTERACTION SYSTEM AND SOMATOSENSORY INTERACTION METHOD", all of which are incorporated herein by reference in their entirety.

TECHNICAL FIELD

The present disclosure relates to a somatosensory interaction system and a somatosensory interaction method based on the somatosensory interaction system.

BACKGROUND

Human-computer interaction technology, such as somatosensory games, is being favored by people for its functions of fitness and entertainment. At present, the human-computer interaction technology is usually achieved by a somatosensory control device connected to a television set, a set-top box or other devices, such as a camera or a game pad. In this case, humans can only interact with the television set in a very limited range, which limits the scope of people's activities and the somatosensory interaction. Moreover, since the somatosensory control device of the prior art has poor accuracy of motion recognition, experience of humans during interaction is further adversely affected.

SUMMARY

In view of the above, it is necessary to provide a somatosensory interaction system and a somatosensory interaction method of the somatosensory interaction system which have higher accuracy of motion recognition and provide better user experience.

A somatosensory interaction system comprises an intelligent electronic device and at least one somatosensory control device wirelessly connected and paired;

the at least one somatosensory control device comprises:
a posture sensing module, wherein the posture sensing module comprises a posture sensor and a posture data processor, the posture sensor is configured to sense motion posture information, the posture data processor is configured to convert the motion posture information in form of electrical signals into digitalized motion posture data;
a transmission module, configured to wirelessly connect and pair the somatosensory control device with the intelligent electronic device and wirelessly transmit the motion posture data to the intelligent electronic device, and
a power supply module, connected to the posture sensing module and the transmission module, respectively, and configured to supply power to the posture sensing module and the transmission module;

the intelligent electronic device comprises:
a data receiving module, wirelessly connected and paired with the transmission module and configured to receive the motion posture data;
an electronic device memory, configured to store the motion posture data, azimuth data of the intelligent electronic device, preset motion parameters and preset motion corresponding to the preset motion parameters, and
an electronic device controller, comprising a calibration unit, a motion recognition unit, and an operation execution unit connected in sequence, the calibration unit is configured to calibrate the motion posture data according to the azimuth data to obtain relative motion posture data of the somatosensory control device with respect to the intelligent electronic device, the motion recognition unit is configured to recognize motion corresponding to the relative motion posture by comparing the relative motion posture data with the preset motion parameters, the operation execution unit is configured to perform corresponding operations according to the recognized motion.

A somatosensory interaction method based on the somatosensory interaction system as described above comprises following steps:
wirelessly connecting and pairing the somatosensory control device with the intelligent electronic device;
defining an initial azimuth, comprising: pointing the somatosensory control device to a preset azimuth, sensing azimuth information of the somatosensory control device at the preset azimuth as initial azimuth data for sensing posture data, and transmitting the initial azimuth data to the intelligent electronic device;
sensing motion and gathering motion posture data by the somatosensory control device;
transmitting the motion posture data to the intelligent electronic device;
calibrating the motion posture data according to the initial azimuth data, to obtain relative motion posture data of the motion posture data with respect to the initial azimuth data;
recognizing actual motion according to the relative motion posture data by the intelligent electronic device, and
outputting, by the intelligent electronic device, instructions according to the actual motion recognized to perform corresponding operations.

A somatosensory interaction method of the somatosensory interaction system as described above comprises following steps:
wirelessly connecting and pairing the somatosensory control device with the intelligent electronic device;
sensing motion and gathering motion posture data by the somatosensory control device;
transmitting the motion posture data to the intelligent electronic device;
sensing azimuth data of the intelligent electronic device;
calibrating the motion posture data according to the azimuth data, to obtain relative motion posture data of the somatosensory control device with respect to the intelligent electronic device;
recognizing actual motion according to the relative motion posture data by the intelligent electronic device, and
outputting, by the intelligent electronic device, instructions according to the actual motion recognized to perform corresponding operations.

By sensing motion posture data via the somatosensory control device, and establishing relative position relationship between the somatosensory control device and the intelligent electronic device to calibrate the motion posture data, the somatosensory control system and somatosensory control method of the present disclosure can avoid error of motion recognition or even false motion recognition due to variations of azimuth when simply using the motion posture data for motion recognition and can obtain more accurate motion posture sensing data, so that the intelligent electronic device can more accurately recognize motion according to the relative motion posture data, thereby improving the accuracy of motion recognition of the somatosensory interaction system. In addition, as the relative position between the somatosensory control device and the intelligent electronic device is determined by the system in real time, the user of the somatosensory control device can perform motion and recognize motion with the intelligent electronic device as reference in real time, thereby improving user experience.

SYMBOL DESCRIPTION

TABLE 1

| | |
|---|---|
| somatosensory interaction system | 100 |
| somatosensory control device | 10 |
| posture sensing module | 12 |
| posture sensor | 120 |
| posture data processor | 122 |
| data filtering unit | 1220 |
| posture analysis unit | 1222 |
| data fusion unit | 1224 |
| data conversion unit | 1226 |
| transmission module | 14 |
| data transmission unit | 140 |
| data transmission controller | 142 |
| data transmission and storage unit | 144 |
| power supply module | 16 |
| battery | 160 |

TABLE 1-continued

| | |
|---|---|
| charging circuit | 162 |
| power management circuit | 164 |
| somatosensory control device body | 18 |
| intelligent electronic device | 20 |
| data receiving module | 22 |
| electronic device memory | 24 |
| electronic device controller | 26 |
| azimuth sensor | 28 |

The present disclosure will be further illustrated by the following detailed description with the accompanying drawings.

DETAILED DESCRIPTION OF DISCLOSED EMBODIMENTS

The somatosensory interaction system and the somatosensory interaction method of the somatosensory interaction system of the present disclosure will be described in further detail below with reference to accompanying drawings and specific examples.

Figure 1:
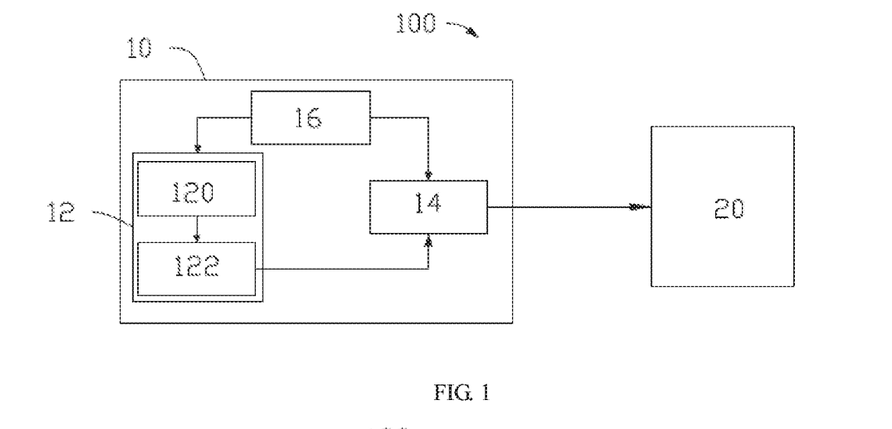
FIG. 1 is a block diagram illustrating connection of elements of the somatosensory interaction system according to the first embodiment of the present disclosure.

Referring to FIG. 1, the first embodiment of the present disclosure provides a somatosensory interaction system 100, comprising a somatosensory control device 10 and an intelligent electronic device 20. The somatosensory control device 10 wirelessly communicates and interacts with the intelligent electronic device 20.

The somatosensory control device 10 is configured to sense static azimuth information and motion posture information. The somatosensory control device 10 comprises a posture sensing module 12, a transmission module 14, and a power supply module 16.

The posture sensing module 12 comprises a posture sensor 120 and a posture data processor 122. The posture sensor 120 is configured to sense physical motion posture information. Generally, the motion posture information is presented in form of electrical signals. The posture sensor 120 may comprise a plurality of sensors for sensing different types of motion posture parameters. In this embodiment, the posture sensor 120 can be a nine-axis sensor, comprising a three-axis acceleration sensor, a three-axis gyro sensor and a three-axis geomagnetic sensor. The nine-axis sensor itself is set with a three-dimensional coordinate system for collecting information of acceleration, angular velocity and a magnetic azimuth of motion posture in a three-dimensional space.

Figure 2:
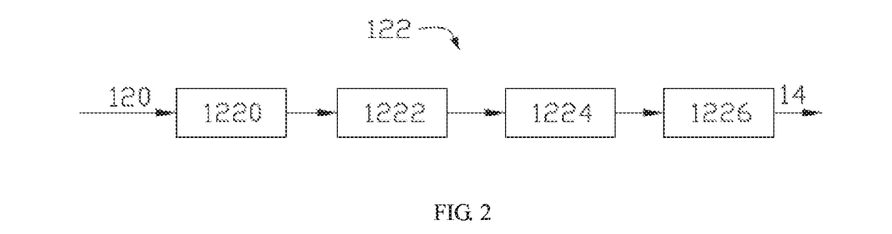
FIG. 2 is a block diagram illustrating connection of elements of the posture data processor of the somatosensory interaction system according to the first embodiment of the present disclosure.

Referring to FIG. 2, the posture data processor 122 can be a microcontroller unit (MCU), configured to receive and process the motion posture information sensed by the posture sensor 120 to obtain motion posture data. Specifically, the posture data processor 122 is configured to convert the posture information in form of electrical signals into digitalized information (the motion posture data). Preferably, the posture data processor 122 comprises a data filtering unit 1220, a posture analysis unit 1222 and a data fusion unit 1224 connected in sequence. The data filtering unit 1220 is configured to filter the motion posture information sensed by the posture sensor 120 to remove noise signals. The data filtering unit 1220 can be implemented by a common filter, its filtering method can be, but not limited to, Kalman filtering. The posture analysis unit 1222 is configured to receive and analyze the filtered motion posture information to obtain initial motion posture data. The initial motion posture data comprises initial acceleration, initial angular velocity and an initial magnetic azimuth. The data fusion unit 1224 is configured to perform inter-calibration on the initial motion posture data according to mutual relationship between the initial motion posture data to obtain secondary motion posture data. The data fusion method can be, but not limited to, a self-adaptive Kalman data fusion algorithm. Generally, there are some drawbacks when using a three-axis acceleration sensor, a three-axis gyro sensor and a three-axis geomagnetic sensor alone to sense motion posture. For example, the acceleration sensor cannot establish absolute or relative heading and is greatly sensitive to motion; the gyro sensor generally cannot provide absolute reference, and its zero position offset drifts with time; the main problem of the three-axis geomagnetic sensor is that it would measure all magnetic fields including Earth's magnetic field, thereby interfering sensing results. The data fusion unit 1224 combines advantages of the three-axis acceleration sensor, the three-axis gyro sensor and the three-axis geomagnetic sensor and adjusts sensed data to each other to obtain more accurate motion posture data. For example, the three-axis acceleration sensor and the three-axis geomagnetic sensor can be used in combination to solve the problem of no absolute reference and zero position offset of the three-axis gyro sensor, in order to provide a long-term absolute reference of heading, pitch and rolling for the three-axis gyro sensor.

Furthermore, the posture data processor 122 may comprise a data conversion unit 1226 for converting the initial motion posture data or the secondary motion posture data to absolute motion posture data with respect to the ground surface.

The posture data processor 122 and the posture sensor 120 are integrally provided, in other words, the posture data processor 122 and the posture sensor 120 are integrally packaged in a same chip, thereby reducing volume and power consumption.

Figure 3:
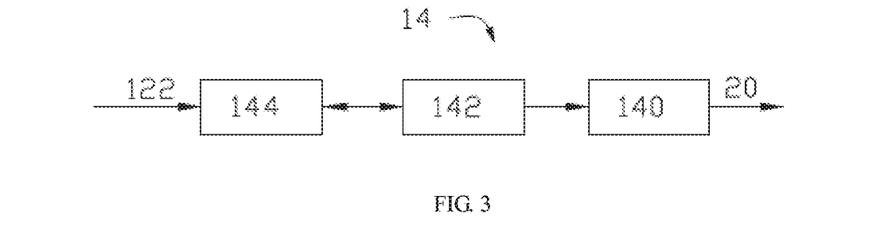
FIG. 3 is a block diagram illustrating connection of elements of the transmission module of the somatosensory interaction system according to the first embodiment of the present disclosure.

Referring to FIG. 1 and FIG. 3, the transmission module 14 is configured to achieve wireless interaction and pairing between the somatosensory control device 10 and the intelligent electronic device 20, and to transmit the motion posture data (absolute motion posture data in the embodiments of the present disclosure) to the intelligent electronic device 20 for recognizing and processing. The transmission module 14 comprises a data transmission unit 140 and a data transmission controller 142. The data transmission unit 140 is configured to receive the motion posture data outputted by the posture sensing module 12 and transmit the motion posture data to the intelligent electronic device 20. The data transmission controller 142 is connected to the data transmission unit 140 to control data transmission of the data transmission unit 140. By especially providing the independent data transmission controller 142 to control data transmission of the data transmission unit 140, efficient and rapid data transmission can be realized, thus accuracy and real-time property of subsequent motion recognition are improved.

The data transmission unit 140 may be at least one of a wireless communication unit, an infrared unit and a Bluetooth unit. In this embodiment of the present disclosure, the data transmission unit 140 is a low-energy Bluetooth (BLE) unit and is compatible to Bluetooth (BT) technological standards, and thus can adapt to be connected to different electrical devices to realize data transmission.

Furthermore, the transmission module 14 comprises a data transmission and storage unit 144, configured to store the motion posture data transmitted by the posture sensing module 12. The data transmission and storage unit 144 is implemented by a flash RAM.

Preferably, the data transmission unit 140, the data transmission controller 142 and the data transmission and storage unit 144 are integrated in a same chip to reduce volume and power consumption. In the embodiment of the present disclosure, the data transmission unit 140, the data transmission controller 142 and the data transmission and storage unit 144 form an integrated circuit chip.

Figure 4:
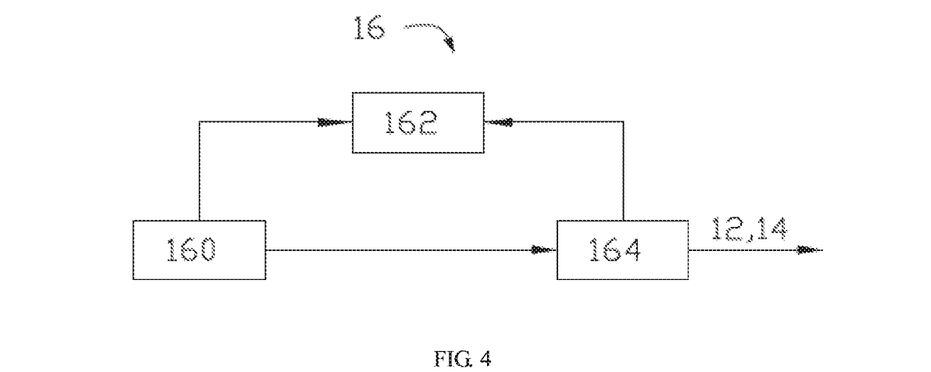
FIG. 4 is a block diagram illustrating connection of elements of the power supply module of the somatosensory interaction system according to the first embodiment of the present disclosure.

Referring to FIG. 1 and FIG. 4, the power supply module 16 is connected to the posture sensing module 12 the transmission module 14 and is configured to supply power thereto. The power supply module 16 may comprise a battery 160, a charging circuit 162 and a power management circuit 164. The battery 160 supplies power to the posture sensing module 12 and the transmission module 14. The battery is not limited to a particular type, but is preferably a secondary battery, such as lithium ion battery, more preferably, a micro secondary battery, such as a button battery.

The charging circuit 162 is configured to charge the battery 160. The power management circuit 164 is configured to control power supplying and charging of the battery 160. Moreover, the power management circuit 164 can adjust power output of the battery 160 according to usage environment and working conditions of the somatosensory control device 10, thus different power consumption modes are realized. For example, when the somatosensory control device 10 is in the standby mode, the power management circuit 164 controls the somatosensory control device 10 to enter a low-power-consumption mode, thereby effectively prolonging usage time of the battery 160.

The posture sensing module 12, the transmission module 14 and the power supply module 16 can be integrally provided on a flexible circuit board to form a micro somatosensory control device 10. As the somatosensory control device 10 can be very small in size, and have a volume ranged from 2 $cm^3$ to 7 $cm^3$, thus the somatosensory control device 10 is readily suitable for various environments where motion postures need to be sensed.

Furthermore, the somatosensory control device 10 comprises an alerting means (not shown in the drawings) configured to alert the user of the somatosensory control device 10 of incoming call, an alarm, low battery and others. The alerting means may be at least one of a vibrator, a sound generator and an alerting lamp.

Figure 5:
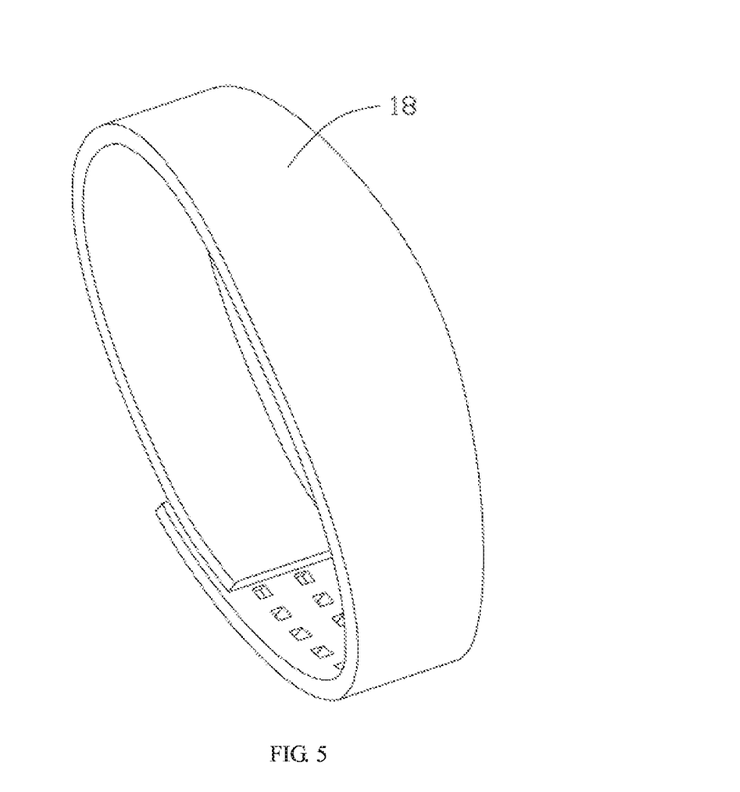
FIG. 5 is a schematic structural view of the bracelet-like somatosensory control device according to the first embodiment of the present disclosure.

Referring to FIG. 5, the somatosensory control device 10 may further comprise a body 18, the somatosensory control device body 18 acts as a packaging structure for packaging each module of the somatosensory control device 10. Preferably, the somatosensory control device body 18 can be a wearable structure, such as a bracelet, a foot ring, a wristband or a finger ring. In the embodiment of the present disclosure, the somatosensory control device 10 is a bracelet. In addition, the somatosensory control device body 18 can also be an affixing structure, such as an affixing body.

The somatosensory control device 10 can be supported by a carrier, and can sense static and dynamic motion postures of the carrier. Any carrier capable of moving can be applied to the present disclosure. For example, the carrier can be, but not limited to, an organism or an exercise machine. The somatosensory control device 10 can be supported by the carrier by various means, including but not limited to wearing, affixing or embedding. In the embodiment of the present disclosure, the carrier is a human, the somatosensory control device 10 can be worn or held by hand by a user, or be affixed to a user to sense motion postures of the user.

In the somatosensory control device 10 of the present disclosure, the posture sensor 122 is provided to exclusively process the motion posture data sensed by the posture sensor 120, and at the same time, the data transmission controller 142 is provided to exclusively control data transmission of the motion posture data of the data transmission unit 140, thus the rates of sensing, analysis and transmission of motion posture data are greatly improved, inaccuracy of motion recognition due to delays is reduced, accordingly, motion posture sensing sensitivity and real-time property of the somatosensory control device 10 are improved and user experience is better.

The intelligent electronic device 20 and the somatosensory control device 10 are separated and mutually independent in a physical space. "Mutually independent" means that the intelligent electronic device 20 and the somatosensory control device 10 can be used independently from each other and perform respective functions. The somatosensory control device 10 can be mounted on or supported by a moving carrier, the intelligent electronic device 20 is configured to monitor or process motion posture data of the moving carrier sensed by the somatosensory control device 10. The intelligent electronic device 20 wirelessly interacts with and is paired with the somatosensory control device 10 via the transmission module 14. The intelligent electronic device 20 has the following functions: (1) receiving the motion posture data; (2) recognizing motion according to the motion posture data; (3) performing corresponding operations according to the recognized motion.

Figure 6:
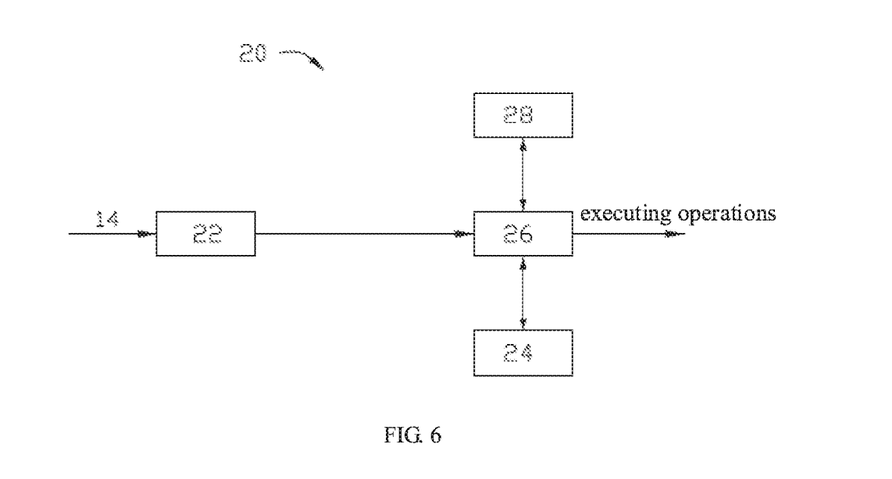
FIG. 6 is a block diagram illustrating connection of elements of the intelligent electronic device of the somatosensory interaction system according to the first embodiment of the present disclosure.

Referring to FIG. 6, the intelligent electronic device 20 comprises a data receiving module 22, an electronic device memory 24 and an electronic device controller 26. The data receiving module 22 is paired with the transmission module 14 and configured to receive the motion posture data transmitted by the transmission module 14 and transmit the motion posture data to the electronic device controller 26. The data receiving module 22 can be a wireless module, such as a Bluetooth, infrared or 3G/4G communication module. The electronic device memory 26 is configured to store preset motion parameters and preset motion corresponding to the preset motion parameters and operation instructions. Furthermore, the electronic device memory 26 may further comprise programs or software operated by the motion. The programs or software can be, but not limited to, control programs of the intelligent electronic device 20, game programs and exercise and fitness programs.

The electronic device controller 26 is configured to convert the received motion posture data into motion recognition parameters corresponding to the format of motion parameters, and compare the motion recognition parameters with the preset motion parameters to recognize motion, and search corresponding operation instructions according to the recognized motion.

Furthermore, the intelligent electronic device 20 comprises an azimuth sensor 28 for sensing azimuth data of the intelligent electronic device 20. The azimuth sensor 28 can cooperate with the posture sensor 120 to obtain relative position between the somatosensory control device 10 and the intelligent electronic device 20. The azimuth sensor 28 may be at least one of a position sensor (such as a geomagnetic sensor), GPS and a network communication module. The intelligent electronic device 20 is preferably a portable electronic device, including but not limited to a mobile phone, an intelligent television, a tablet computer or a laptop computer.

Preferably, the electronic device controller 26 comprises a calibration unit, a motion recognition unit and an operation execution unit connected in sequence. The calibration unit is configured to calibrate the motion posture data according to the azimuth data of the intelligent electronic device 20 to obtain relative motion posture data of the somatosensory control device 10 with respect to the intelligent electronic device 20. The motion recognition unit is configured to recognize motion corresponding to the relative motion posture by comparing the relative motion posture data with the preset motion parameters. The operation execution unit is configured to perform corresponding operations according the recognized motion.

Furthermore, the intelligent electronic device 20 comprises a display (not shown in the drawings) for displaying operation instructions or motion.

Figure 7:
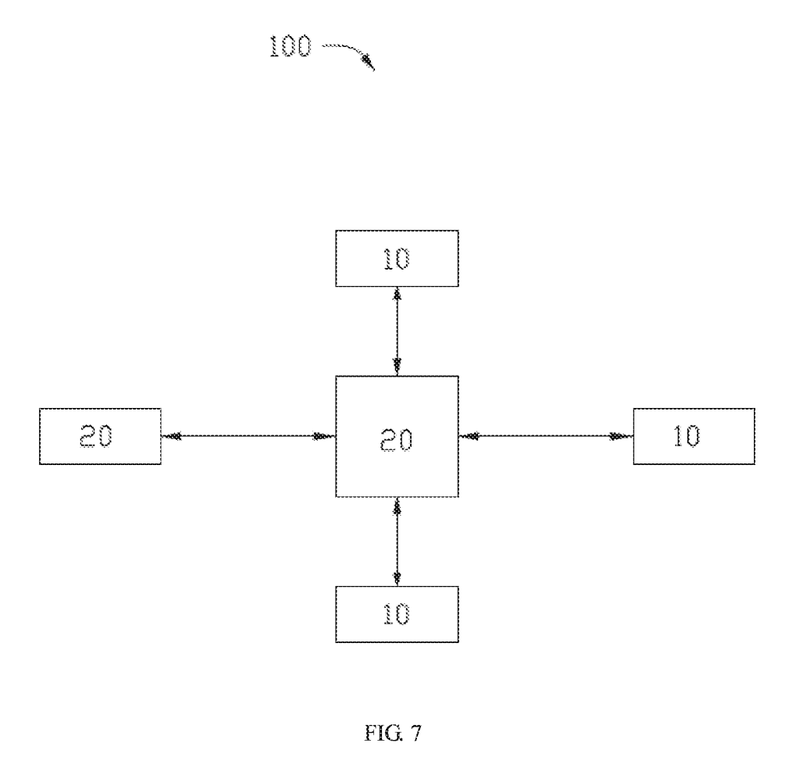
FIG. 7 is a block diagram illustrating connection of elements of the somatosensory interaction system according to another embodiment of the present disclosure.

Referring to FIG. 7, the somatosensory interaction system 100 may further comprise a plurality of the somatosensory control devices 10, the plurality of somatosensory control devices 10 can be provided on different carriers or at different locations of a same carrier. The plurality of somatosensory control devices 10 can interact and be paired with the intelligent electronic device 20 via respective transmission module 14, thus recognition of the motion posture data sensed by the plurality of somatosensory control devices 10 can be realized simultaneously or in turn.

Figure 8:
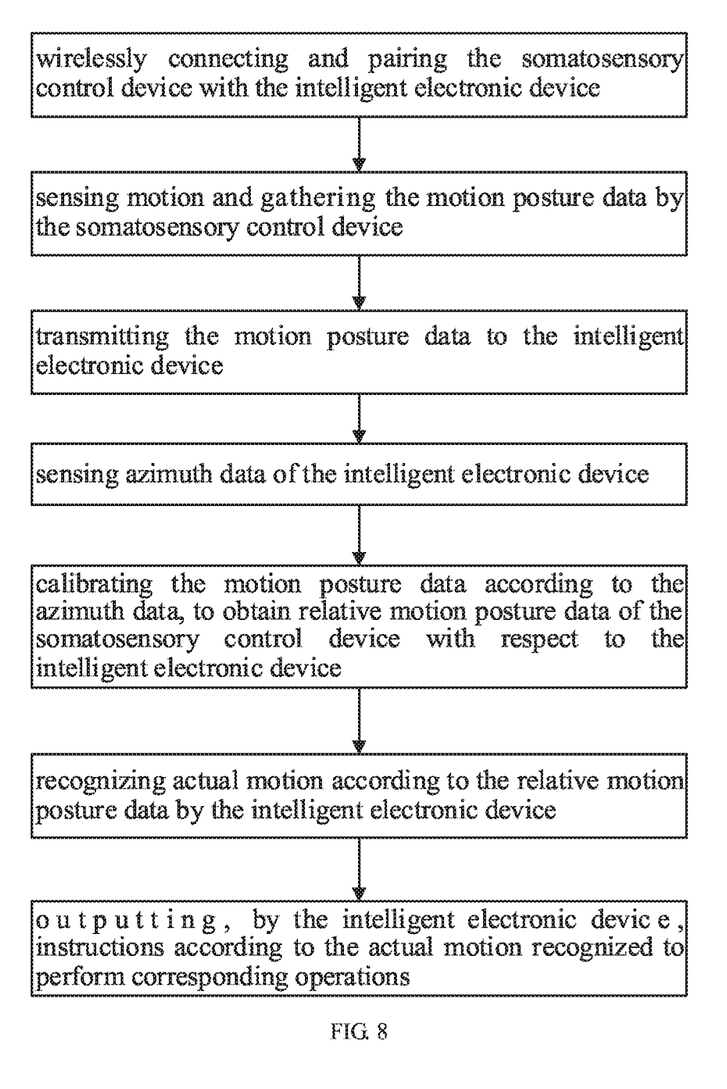
FIG. 8 is a flowchart illustrating the somatosensory interaction method of the somatosensory interaction system according to the second embodiment of the present disclosure.

Referring to FIG. 8, the second embodiment of the present disclosure further provides a somatosensory interaction method of the somatosensory interaction system 100, the method comprises following steps:

S1, pairing the somatosensory control device 10 with the intelligent electronic device 20;

S2, sensing motion and gathering motion posture data by the somatosensory control device 10;

S3, transmitting the motion posture data to the intelligent electronic device 20;

S4, sensing azimuth data of the intelligent electronic device 20;

S5, calibrating the motion posture data according to the azimuth data to obtain relative motion posture data of the somatosensory control device 10 with respect to the intelligent electronic device 20;

S6, recognizing actual motion according to the relative motion posture data by the intelligent electronic device 20, and S7, outputting, by the intelligent electronic device 20, instructions according to the actual motion recognized to perform corresponding operations.

In the above step S1, connection, recognition and pairing between the somatosensory control device 10 and the intelligent electronic device 20 can be accomplished via Bluetooth, infrared and wireless network.

The above step S2 may further comprise:

S21, sensing the motion posture information by the somatosensory control device 10 via the posture sensor 120;

S22, filtering, performing posture analysis and data fusion on the motion posture information by the posture data processor 122 to obtain secondary motion posture data, and S23, converting the secondary motion posture data to absolute motion posture data with respect to the ground surface.

In the above step S22, the motion posture information and the secondary motion posture data are obtained based on three-dimensional coordinate axes, which are established by the posture sensor 120 with itself as the origin. Absolute motion posture data with respect to the ground surface can be obtained by data conversion in the step S23. The motion posture data with higher accuracy can be obtained by data fusion. The filtering, posture analysis and data fusion method can be implemented by common motion data processing algorithms. In the embodiment of the present disclosure, the motion posture data is absolute motion posture data.

In the above step S2, the type of the motion posture data depends on the type of the posture sensor 120. As mentioned above, in the embodiment of the present disclosure, the motion posture data comprises acceleration, angular velocity and a geomagnetic azimuth of the somatosensory control device 10 in a three-dimensional space.

The above step S2 may further comprise sensing a plurality of the motion posture data, and then combining the plurality of data to obtain the final motion posture data. In the embodiment of the present disclosure, up to 100 groups of the motion posture data can be obtained in one second.

After receiving the motion posture data, the above step S3 may further comprise: filtering the motion posture data by the intelligent electronic device 20. Noise signals can be further filtered by the intelligent electronic device 20 so as to obtain more accurate motion posture data.

In the above step S4, the intelligent electronic device 20 can use the azimuth sensor 28 to sense an azimuth of the intelligent electronic device 20 to obtain the azimuth data.

The above step S5 aims to obtain the relative position between the somatosensory control device 10 and the intelligent electronic device 20 and thus to obtain the relative motion posture data of the somatosensory control device 10 with respect to the intelligent electronic device 20. In the embodiment of the present disclosure, the relative motion posture data comprises a relative motion direction, relative acceleration and relative angular velocity. The acceleration and the angular velocity are vector data, and the relative acceleration and the relative angular velocity are obtained by calibrating the direction of the acceleration and the angular velocity with the azimuth data of the intelligent electronic device 20. The relative motion posture data can be used to better indicate relative position between user (carrier) of the somatosensory control device 10 and the intelligent electronic device 20, thus user experience and sensitivity and accuracy of data processing can be improved.

The above step S6 further comprises:

S61, converting the relative motion posture data into motion recognition parameters corresponding to the format of motion parameters;

S62, reading preset motion parameters and preset motion corresponding to the preset motion parameters;

S63, comparing the motion recognition parameters and the preset motion parameters to obtain a motion output result, and S64, recognizing actual motion according to the motion output result.

The relative motion posture data includes angular velocity, acceleration and a geomagnetic azimuth and other information. For example, in some cases, these data shows that one action of a certain magnitude of force occurs at a direction. This is the purpose of data conversion in step S61. The motion recognition parameters can be multiple-dimension arrays and the multiple-dimension arrays comprise a plurality of different types of motion definition standards, such as direction and magnitude of force. The motion recognition parameters have special purposes in different specific applications, and the motion recognition parameters can vary according to different purposes.

The intelligent electronic device 20 stores preset motion recognition parameters and preset motion or motion performing standards corresponding to the motion recognition parameters. By comparing the motion recognition parameters with the preset motion parameters, actual motion or motion standards (motion output results) corresponding to the motion recognition parameters, such as magnitude of force, can be obtained.

In the above step S7, the intelligent electronic device 20 outputs instructions according to the corresponding motion or the motion standards to perform corresponding operations. The instruction can drive hardware or software of the intelligent electronic device 20 to execution operations, for example, allow the intelligent electronic device 20 to execute or display corresponding program instructions or motion (such as, game, fitness applications, rehabilitation applications), control and operate a mouse, a keyboard or a touchscreen. Correspondingly, the operations can be mouse operations, keyboard operations, touchscreen operations, operations of application programs, game operations and display.

By sensing motion posture data via the somatosensory control device 10, and establishing relative position relationship between the somatosensory control device 10 and the intelligent electronic device 20 to calibrate the motion posture data, the somatosensory interaction system 100 and the somatosensory interaction method of the somatosensory interaction system 100 according to the first and second embodiments of the present disclosure can avoid error of motion recognition or even false motion recognition due to variations of azimuth when simply using the motion posture data for motion recognition and can obtain more accurate motion posture sensing data, so that the intelligent electronic device 20 can obtain more accurate motion according to the relative motion posture data, thereby improving the accuracy of motion recognition of the somatosensory interaction system 100. In addition, as the relative position between the somatosensory control device 10 and the intelligent electronic device 20 is determined by the system in real time, the user of somatosensory control device 10 can perform motion and recognize motion with the intelligent electronic device 20 as reference in real time, the user experience is improved.

Figure 9:
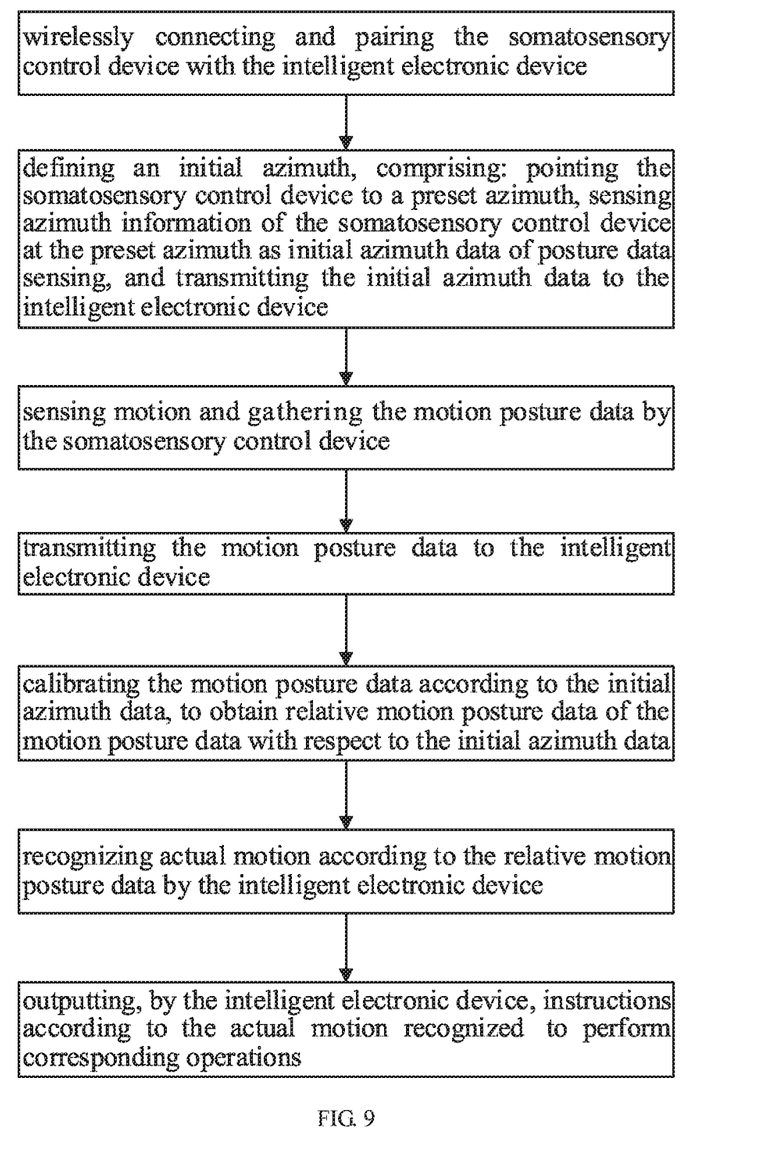
FIG. 9 is a flowchart illustrating the somatosensory interaction method of the somatosensory interaction system according to the third embodiment of the present disclosure.

Referring to FIG. 9, the third embodiment of the present disclosure provides a somatosensory interaction method of the somatosensory interaction system 100, the method comprises following steps:

B1, paring the somatosensory control device 10 with the intelligent electronic device 20;

B2, defining an initial azimuth, comprising: pointing the somatosensory control device 10 to a preset azimuth, sensing azimuth information of the somatosensory control device 10 at the preset azimuth as initial azimuth data for sensing posture data, and transmitting the initial azimuth data to the intelligent electronic device 20;

B3, sensing motion and gathering motion posture data by the somatosensory control device 10;

B4, transmitting the motion posture data to the intelligent electronic device 20;

B5, calibrating the motion posture data according to the initial azimuth data to obtain relative motion posture data of the motion posture data with respect to the initial azimuth data;

B6, recognizing actual motion by the intelligent electronic device 20 according to the relative motion posture data, and B7, outputting instructions by the intelligent electronic device 20 to perform corresponding operations.

The somatosensory interaction method according to the third embodiment of the present disclosure is substantially the same as the somatosensory interaction method according to the second embodiment, except that the somatosensory interaction method according to the third embodiment is directed to motion recognition of the intelligent electronic device 20 without an azimuth sensor.

In the above step B2, the initial azimuth is set according to the location of the intelligent electronic device 20, thus the relative position between the somatosensory control device 10 and the intelligent electronic device 20 can be subsequently determined. Preferably, the preset azimuth is an azimuth towards the intelligent electronic device 20. More preferably, the preset azimuth is facing towards the intelligent electronic device 20.

In the above step B2, the initial azimuth data can be sensed by a geomagnetic azimuth sensor of the somatosensory control device 10. Further, the somatosensory control device 10 converts the initial azimuth data into azimuth data with respect to the ground surface.

In the above step B5, when the initial azimuth is an azimuth of the intelligent electronic device 20, relative position between the somatosensory control device 10 and the intelligent electronic device 20 can be obtained, thereby making interaction between the somatosensory control device 10 and the intelligent electronic device 20 more convenient and providing better experience of interaction.

The other steps of the somatosensory interaction method according to the third embodiment of the present disclosure are substantially the same as the corresponding steps of the somatosensory interaction method according to the second embodiment, specifically, the step B1 is the same as the step S1, the step B3 is the same as the step S2, the step B4 is the same as the step S3, the steps B6-B7 are the same as the steps S6-S7. The details will not be repeated herein.

By defining an initial azimuth, and calibrating motion posture data sensed by somatosensory control device 10 with the initial azimuth, the somatosensory interaction method according to the third embodiment of the present disclosure can avoid error of motion recognition or even false motion recognition due to variations of azimuth when simply using the motion posture data for motion recognition, thereby effectively improving the accuracy of motion recognition of the intelligent electronic device 20. In addition, as the relative position between the somatosensory control device 10 and the intelligent electronic device 20 is determined in real time in the somatosensory interaction method, the user of the somatosensory control device 10 can perform motion and recognize motion with the initial azimuth as reference in real time, thereby improving user experience. Moreover, by defining the initial azimuth, the intelligent electronic device 20 can realize accurate recognition of motion without using an azimuth sensor, thereby greatly expanding selection range of the intelligent electronic device 20.

Figure 10:
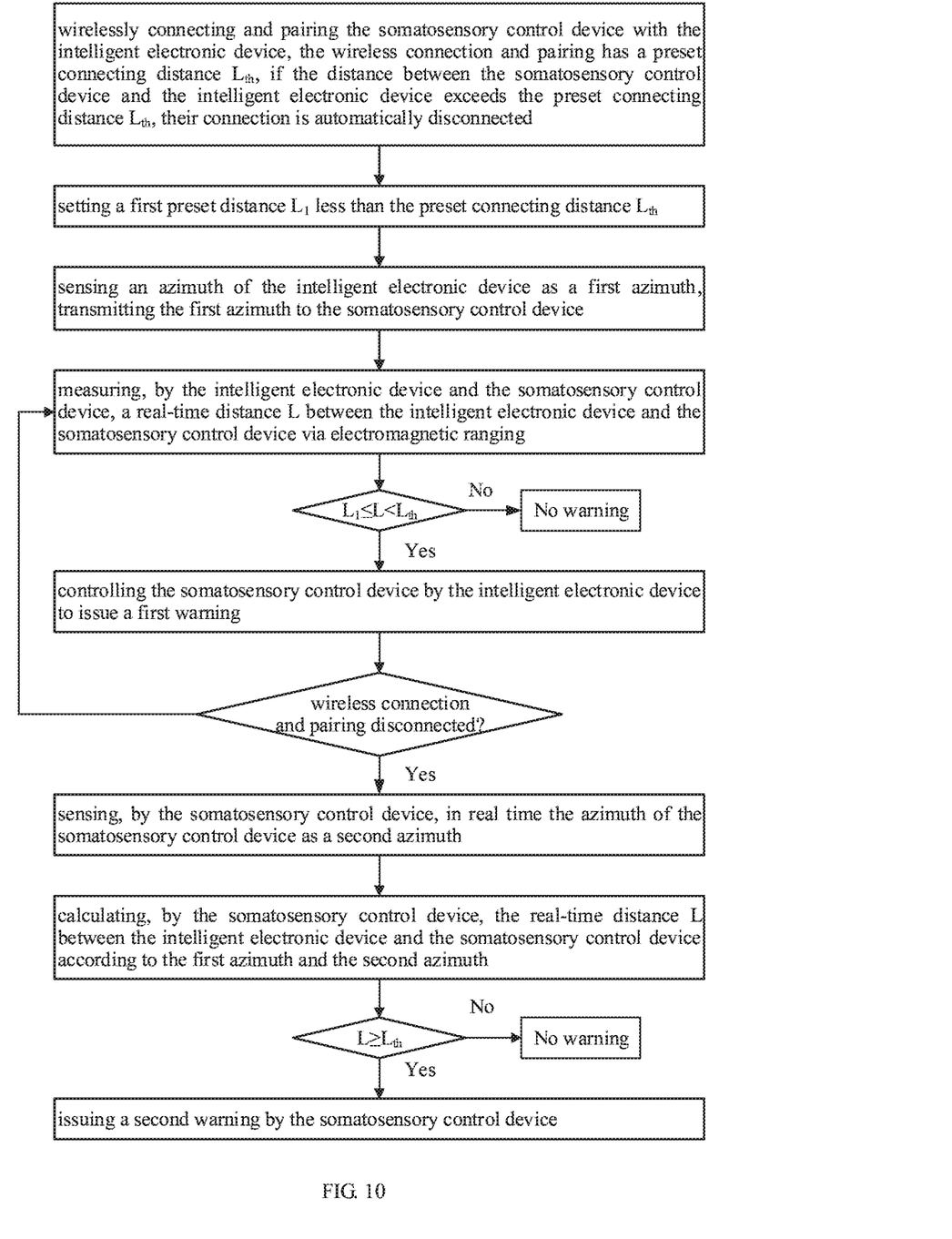
FIG. 10 is a flowchart illustrating the alerting method for preventing losing an intelligent electronic device using a somatosensory control device according to the fourth embodiment of the present disclosure.

Referring to FIG. 10, the fourth embodiment of the present disclosure further provides an alerting method for preventing losing the intelligent electronic device 20 using the somatosensory control device 10, comprising following steps:

C1, wirelessly connecting and pairing the somatosensory control device 10 with the intelligent electronic device 20, the wireless connection and pairing has a preset connecting distance $L_{th}$, if the distance between the somatosensory control device 10 and the intelligent electronic device 20 exceeds the preset connecting distance $L_{th}$, their connection is automatically disconnected;

C2, setting a first preset distance $L_1$ less than the preset connecting distance $L_{th}$;

C3, sensing an azimuth of the intelligent electronic device 20 as a first azimuth, transmitting the first azimuth to the somatosensory control device 10;

C4, measuring, by the intelligent electronic device 20 and the somatosensory control device 10, a real-time distance L between the intelligent electronic device 20 and the somatosensory control device 10 via electromagnetic ranging, if $L_1 \leq L < L_{th}$, controlling the somatosensory control device 10 by the intelligent electronic device 20 to issue a first warning;

C5, when the wireless pairing and connection is disconnected, sensing, by the somatosensory control device 10, in real time the azimuth of the somatosensory control device 10 as a second azimuth, and C6, calculating, by the somatosensory control device 10, the real-time distance L between the intelligent electronic device 20 and the somatosensory control device 10 according to the first azimuth and the real-time second azimuth, if $L \geq L_{th}$, issuing a second warning by the somatosensory control device 10.

In the above step C1, the wireless connection and pairing as mentioned above can be Bluetooth connection or infrared connection. In the embodiment of the present disclosure, the wireless connection and pairing is Bluetooth connection. The Bluetooth and infrared generally have a certain connecting and pairing distance range, if exceeding the range, the connection is automatically disconnected. The preset connecting distance $L_{th}$ is a maximum distance at or within which the somatosensory control device 10 can be connected to the intelligent electronic device 20.

In the above step C2, the first preset distance $L_1$ is close to and less than the preset connecting distance $L_{th}$, so that when the somatosensory control device 10 is to be disconnected with the intelligent electronic device 20, the somatosensory control device 10 can remind that the distance between the user and the intelligent electronic device 20 is beyond safe range, and remind the user whether he/she forgot to carry the intelligent electronic device 20. The relationship between the first preset distance $L_1$ and the preset connecting distance $L_{th}$ is preferably: $L_1:L_{th}=6\text{-}9.5:10$.

In the above step C3, the somatosensory control device 10 receives azimuth information of the intelligent electronic device 20, so that during later stages, even when the wireless connection between the somatosensory control device 10 and the intelligent electronic device 20 is disconnected, the somatosensory control device 10 can obtain the distance between the somatosensory control device 10 and the intelligent electronic device 20 according to its own azimuth information and the azimuth information of the intelligent electronic device 20, and then can remind the user whether or not the intelligent electronic device 20 is left.

In the above step C4, when the real-time distance L between the intelligent electronic device 20 and the somatosensory control device 10 is inside range of the preset connecting distance $L_{th}$, the distance L is measured according to wireless connection mode of the intelligent electronic device 20 and the somatosensory control device 10. As mentioned above, the wireless connection mode can be Bluetooth connection or infrared connection, correspondingly, the ranging method can be Bluetooth ranging or infrared ranging. The Bluetooth ranging and the infrared ranging can adopt the same electromagnetic ranging principle, in other words, the distance can be measured according to transmission time difference between sending signals and receiving signals. The first warning may be warning sound or warning vibration of the somatosensory control device 10.

In the above step C5, the somatosensory control device 10 can use the transmission module 14 to sense whether the wireless pairing is connected or disconnected, when detecting that the wireless pairing is disconnected, the somatosensory control device 10 senses in real time the current azimuth of the somatosensory control device 10 so as to subsequently re-determine the real-time distance L between the somatosensory control device 10 and the intelligent electronic device 20. In the embodiment, the somatosensory control device 10 can realize this just by using the geomagnetic sensor.

In the above step C6, by re-determining the real-time distance L between the intelligent electronic device 20 and the somatosensory control device 10, sensing accuracy can be improved, false alarms caused by manual closing of wireless pairing can be prevented, thus the alarming sensitivity and accuracy of the somatosensory control device 10 can be improved. If $L \geq L_{th}$, the somatosensory control device 10 issues a second warning, the second warning has the same form as the first warning, but has greater intensity to again remind the user that the intelligent electronic device 20 is outside of safe distance range.

In the alerting method for prevent losing the intelligent electronic device 20 using the somatosensory control device 10 according to the fourth embodiment of the present disclosure, when the wireless connection and pairing is established, the relative distance between the somatosensory control device 10 and the intelligent electronic device 20 within pairing range can be obtained. The somatosensory control device 10 can utilize the first warning to alert the user about the relative distance between the somatosensory control device 10 and the intelligent electronic device 20. At the same time, when detecting that the wireless connection and pairing is disconnected, the somatosensory control device 10 continues to detect whether the relative distance between the somatosensory control device 10 and the intelligent electronic device 20 exceeds the safe range, if exceeding the safe range, the somatosensory control device 10 issues the secondary warning. Therefore, the method can greatly improve awareness of the user, and significantly reduce the probability of losing the intelligent electronic device.

Finally, it is to be understood that those skilled in the art may make variations to the embodiments within the spirit of the present disclosure, and such variations that follow the spirit of the disclosure are intended to be included within the scope of the disclosure as claimed.

What is claimed is:

1. A somatosensory interaction method of a somatosensory interaction system, wherein the
    somatosensory interaction system comprises an intelligent electronic device and at least one somatosensory control device wirelessly connected and paired, the somatosensory control device is configured to sense motion and gather motion posture data;
    the somatosensory interaction method comprises following steps:
    wirelessly connecting and pairing the somatosensory control device with the intelligent electronic device;
    defining an initial azimuth, comprising: pointing the somatosensory control device to a preset azimuth, sensing azimuth information of the somatosensory control device at the preset azimuth as initial azimuth data for sensing posture data, and transmitting the initial azimuth data to the intelligent electronic device;
    sensing motion and gathering the motion posture data by the somatosensory control device;
    transmitting the motion posture data to the intelligent electronic device;
    calibrating the motion posture data according to the initial azimuth data, to obtain relative motion posture data of the motion posture data with respect to the initial azimuth data;
    recognizing actual motion according to the relative motion posture data by the intelligent electronic device, and
    outputting, by the intelligent electronic device, instructions according to the actual motion recognized to perform corresponding operations.

2. The somatosensory interaction method of claim 1, wherein the preset azimuth is an azimuth towards the intelligent electronic device.

3. The somatosensory interaction method of claim 1, wherein the somatosensory control
    device comprises a posture sensor and a posture data processor, the step of sensing motion and gathering motion posture data further comprises:
    sensing motion posture information by the somatosensory control device via the posture sensor;
        filtering, performing posture analysis and data fusion on the motion posture information by the posture data processor to obtain secondary motion posture data, and
    converting the secondary motion posture data to absolute motion posture data with respect to the ground surface.

4. The somatosensory interaction method of claim 1, wherein the motion posture data is firstly filtered to further remove noise signals after being transmitted to the intelligent electronic device.

5. The somatosensory interaction method of claim 1, wherein the step of recognizing actual motion according to the relative motion posture data by the intelligent electronic device specifically comprises:
    converting the relative motion posture data to motion recognition parameters corresponding
    to format of motion parameters;
    reading the preset motion parameters and the preset motion corresponding to the preset motion parameters; comparing the motion recognition parameters and the preset motion parameters to obtain a motion output result, and recognizing the actual motion according to the motion output result.

6. The somatosensory interaction method of claim 5, wherein the motion recognition parameters are multiple-dimension arrays, the multiple-dimension arrays comprise a plurality of different types of motion definition standards.

7. The somatosensory interaction method of claim 1, wherein the operations comprise
    mouse operations, keyboard operations, touchscreen operations, operations of application programs or game operations and display.

8. The somatosensory interaction method of claim 1, wherein the somatosensory control device is mounted on a moving carrier to sense motion posture data of the moving carrier, the moving carrier is an organism or an exercise machine.

9. The somatosensory interaction method of claim 1, wherein the plurality of somatosensory control devices are wirelessly connected and paired with the intelligent electronic device, respectively, and the intelligent electronic device simultaneously recognizes the motion posture data sensed by the plurality of somatosensory control devices.

* * * * *